United States Patent [19]
Kawamura

[11] Patent Number: 5,771,855
[45] Date of Patent: Jun. 30, 1998

[54] DAMAGE DETECTING APPARATUS FOR CERAMIC PARTS

[75] Inventor: Hideo Kawamura, Samukawa-machi, Japan

[73] Assignee: Isuzu Ceramics Research Institute Co., Ltd., Kanagawa-ken, Japan

[21] Appl. No.: 740,187

[22] Filed: Oct. 28, 1996

[30] Foreign Application Priority Data

Nov. 8, 1995 [JP] Japan ................................. 7-313767
Nov. 8, 1995 [JP] Japan ................................. 7-313768
Nov. 8, 1995 [JP] Japan ................................. 7-313769

[51] Int. Cl.$^6$ .................................................. F02B 77/00
[52] U.S. Cl. .......................... 123/198 D; 123/193.1; 123/668
[58] Field of Search ........................... 123/198 D, 668, 123/193.1

[56] References Cited

FOREIGN PATENT DOCUMENTS 7-158448  6/1995  Japan .

OTHER PUBLICATIONS

Patent Abstract of Japan, vol. 95, No. 001, Jan. 17, 1995, JP–A–07012773.

*Primary Examiner*—Noah P. Kamen
*Attorney, Agent, or Firm*—Browdy and Neimark

[57] ABSTRACT

The damage detecting apparatus for ceramic parts detects breakage of the ceramic combustion chamber structure and valves or breakage and wear of the cylinder liner and minimizes the damages to the structure and valves. The breakage of the head liner forming the ceramic combustion chamber can be detected by arranging the conductive ceramic wires on the outer circumferential surface of the head liner and passing a small current through these wires. The breakage of the valves installed in the ports of the cylinder head can be detected by arranging the conductive lines over the entire length of the valve stem and passing a small current to the conductive lines. The damages to the ceramic cylinder liner, such as wear, can be detected by arranging the conductive lines over the inner wall surface and passing a small current to the conductive lines. The controller, in response to detection signals from the current detector indicating the breakage of wire and the amount of wear, turns on alarm lamps and stops the fuel pump to stop the supply of fuel to the combustion chamber.

22 Claims, 8 Drawing Sheets

DAMAGE DETECTING APPARATUS FOR CERAMIC PARTS

BACKGROUND OF THE INVENTION

1. Field of the Invention

The present invention relates to a damage detecting apparatus for ceramic parts, capable of detecting a damaged state, such as cracks, breaks, fractures and wear, in ceramics structures that form engine components such as combustion chambers, valves and cylinder liners.

2. Description of the Prior Art

In the engine components made of ceramics, such as silicon nitride, there have always been concerns for their reliability and durability. Heat-insulated engines have a head liner—a one-piece assembly consisting of a head portion and a liner portion—installed in a cavity of the cylinder head to form a combustion chamber. Because of a heat insulating air layer formed between the head liner's periphery and the cavity, when the temperature of the head liner increases, the durability of the head liner is not fully guaranteed.

The heat-insulated engines have valves arranged in intake and exhaust ports formed in the cylinder head. When these valves are made of a ceramic material, they are considered likely to develop damages such as cracks, breakage and fracture.

In heat-insulated engines, some cylinder liners, which form a cylinder installed in a hollow portion of the cylinder block, are made of ceramics. Because a piston reciprocates in the cylinder liner, the cylinder liner of a ceramic material is subject to damages such as wear, cracks or breakage. Engines are generally overhauled or inspected at predetermined intervals. If the engine overhaul timing can be determined according to the wear of the cylinder liner, not only can an unnecessary overhaul work be spared but excess wear and breakage of the cylinder liner can be detected early, thereby forestalling possible accidents.

A conventional gas engine used as the cogeneration engine is disclosed in Japan Patent Laid-Open No. 158448/1995. This gas engine has a sub-combustion chamber wall body—which forms a sub-combustion chamber—arranged in a cavity of the cylinder head to form a heat insulating air layer. A head liner of a one-piece structure having a head underside portion and a liner upper portion and forming the main combustion chamber is installed in the cylinder head. A gas chamber communicating with the head portion of the sub-combustion chamber through a throttle portion is formed in a cylinder head. The gas chamber is provided with a gas introducing port to supply a natural gas through a gas passage into the sub-combustion chamber. A control valve is provided which opens a communication hole near the end of the compression stroke. A gas introducing valve that is opened with the communication hole closed is provided at the gas introducing port. In this gas engine, by opening the gas introducing valve installed in the gas chamber, the natural gas is supplied into the gas chamber so that the natural gas can be retained in the gas chamber and near the throttle portion. Hence, the gas engine produces a rich air-fuel mixture in areas near the gas chamber and the throttle portion. In this state, when a pressurized hot air is introduced from the main combustion chamber into the sub-combustion chamber through the communication hole, the mixture near the gas chamber and the throttle portion is ignited reliably, initiating swift propagation of combustion and preventing misfiring. This phenomenon is advantageous particularly during a partial load condition because the retained natural gas near the outlet of the gas chamber assures smooth ignition and combustion.

If the above-mentioned engine using gases and a variety of other fuels is formed as a heat-insulated engine using ceramics, a problem arises. That is, because of hot gases and heat-insulating structures, the ceramics parts are elevated in temperature and thermally loaded or subjected to heat shocks. These in turn may cause damages to the ceramic components, such as cracks, scores and breaks.

In engines, which are expensive and required of more than 10 years of service, like cogeneration engines that use natural gases, the most stringent demands are placed on the reliability of the engine components.

For example, if the engine operation is continued with cracks developed in the combustion chamber structure, the engine performance deteriorates and broken pieces of ceramics may cause damages to other components, leading to destruction of the whole engine, which is costly. The conventional gas engine with ceramics is therefore not sufficiently reliable.

If the engine operation is continued with valves cracked or scored, not only is the engine performance degraded but also broken pieces of ceramic components may damage other parts leading to destruction of the engine. If that happens, the situation cannot be remedied only by the parts replacement, requiring costly service. The damaged components will also result in significant reduction in engine life, pushing up the cost of the cogeneration engine.

Further, if the engine operation is continued without an operator noticing the existence of small damages such as wear, cracks or scores in cylinder liner, not only the cylinder liner but also other engine components are adversely affected, making the engine unrecoverable to normal condition simply by replacing damaged parts, reducing the service life of the engine, which in the case of cogeneration engines means higher cost.

To deal with this situation, when the combustion chamber structure is constructed of ceramic components or the valves formed of ceramic materials, it is desired that small cracks or scores in the combustion chamber structure, which easily develop from the outside thereof, and small cracks in the valves be detected early, allowing the damaged components to be replaced or repaired immediately, thereby avoiding greater damages to the engine and assuring reliability.

The relative sliding motion between the cylinder liner and the piston ring—unlike the simple fluid lubrication that occurs with other components such as engine crankshafts' journals and turbine shafts—involves a boundary lubrication and a fluid lubrication and also a combination of these lubricating conditions and may result in increased wear. If the engine operation is continued with the cylinder liner worn, cracked or scored, not only is the engine performance deteriorated but also broken pieces of ceramics may cause damages to other components. This is costly and degrades reliability, which in turn renders the engine performance unrecoverable to normal simply by parts replacement and shortens the life of the engine. In the cogeneration engine, this translates into higher cost. When the cylinder liner is formed of ceramic components, it is therefore desired that damages to the cylinder liner such as wear and cracks be detected early, allowing the damaged cylinder liner to be replaced immediately, thereby preventing adverse effects from propagating to other engine components and assuring reliability.

SUMMARY OF THE INVENTION

The present invention relates to a damage detecting apparatus for ceramic parts comprising: ceramic structures made of ceramics; wires made of a conductive ceramics and arranged on the ceramic structures; current detectors provided in lines connecting to connection terminals of the wires; current supply means for supplying a small current through the lines to the wires continuously or intermittently; and a controller which, in response to wire break detection signals from the current detectors, turns on alarm lamps and stops the operation of the ceramic structures. The ceramic structures are components of the engine, such as combustion chamber structures, valves and cylinder liners.

This invention relates to a damage detecting apparatus for ceramic parts comprising: ceramic structures made of ceramics; wires made of a conductive ceramics and arranged on the ceramic structures; current detectors provided in lines connecting to connection terminals of the wires; current supply means for supplying a small current through the lines to the wires continuously or intermittently; and a controller which, in response to wire break detection signals from the current detectors, turns on alarm lamps and stops the operation of the ceramic structures. In this invention, the ceramic structures are ceramic parts of the engine, such as combustion chamber structures, valves and cylinder liners.

The damage detecting apparatus for ceramic parts comprises: a ceramic combustion chamber structure installed in a cavity formed in any one of a cylinder head and a cylinder block, the ceramic combustion chamber structure forming a combustion chamber, the combustion chamber forming a cylinder upper surface portion and a part of a cylinder liner; wires made of a conductive ceramics and arranged on the outer circumferential surfaces of the combustion chamber structures; current detectors provided in lines connecting to connection terminals of the wires; current supply means for supplying a small current through the lines to the wires continuously or intermittently; and a controller which, in response to wire break detection signals from the current detectors, turns on alarm lamps and stops the fuel supply to the combustion chamber.

The combustion chamber structure is a head liner of a one-piece structure for the main combustion chamber having a head underside portion and a liner upper portion, the head liner being installed in the cavity of the cylinder head to form a heat insulating air layer. Or the combustion chamber structure is a structure forming a sub-combustion chamber that communicates with the head liner through a communication hole.

The wires arranged on the outer circumferential surface of the combustion chamber structure can be insulated easily with a heat insulating air layer or insulating film formed around the outer circumferential surface of the combustion chamber structure so that no shortcircuits occur on the outer circumferential surface of the combustion chamber structure. The wires are connected at one end to the lines leading to the current detector and at the other end through connection terminals to the metal cylinder head or cylinder block that works as a ground. Further, the wires are insulated by an heat insulating air layer or insulating film over the outer circumferential surface of the combustion chamber structure.

The wires are made of a conductive ceramics containing SiC and at least one of TiC, ZrC, WC, TiN, $ZrB_2$, $TiB_2$, $HfB_2$, $NbB_2$ and $TaB_2$ added to SiC. Or the wires are provided to an outer circumferential surface of the combustion chamber structure by coating or impregnating the conductive ceramics to the outer circumferential surface. The wires can also be formed by embedding powdered metal in a wire portion etched in an outer circumferential surface of the combustion chamber structure.

The sensitivity of the wires can be controlled by the ratio of an additive $ZrB_2$ to the base material SiC to which it is added. For example, by changing the amount of $ZrB_2$ added to SiC, the temperature coefficient of resistance changes from a positive to a negative value. That is, when the amount of $ZrB_2$ added to SiC is set to about 30%, the wires will not easily pass current at elevated temperatures. When the amount of the additive is set at around 10%, the wires will easily pass current at elevated temperatures, enhancing the detection sensitivity.

The wires on the outer circumferential surface of the combustion chamber structure may be formed 10–20 $\mu$m thick and several millimeters wide. Two or more wires may be formed spaced apart on the outer circumferential surface of the combustion chamber structure. In that case, connecting these wires in series allows a wider area of the combustion chamber structure to be monitored.

The method of forming wires over the outer circumferential surface of the combustion chamber structure involves sintering a combustion chamber structure made of ceramics such as silicon nitride, machining the sintered structure, applying conductive ceramic powder to the outer circumferential surface of the combustion chamber structure, and then sintering the structure again. Alternatively, the wires may be formed by applying or impregnating the conductive ceramics powder to the formed combustion chamber structure made of ceramics such as silicon nitride and then sintering it.

Because the damage detecting apparatus for ceramic parts is constructed as described above, when a damage to the combustion chamber structure such as crack or score occurs, a wire break detection signal is issued from the current detector to turn on an alarm lamp, allowing an operator to detect the trouble early and replace or repair the damaged portion of the combustion chamber structure. This in turn minimizes adverse effects on other components, improving durability, reliability and service life of the engine, reducing the overall cost. Hence, the combustion chamber structure having the damage detecting apparatus is advantageously applied to the cogeneration engines.

Further, in an engine having ceramic valves of one-piece structure which open and close ports formed in a cylinder head and comprise valve stems arranged to reciprocate along valve guides provided in the cylinder head and valve heads integrally formed with, the valve stems; the damage detecting apparatus for ceramic parts comprises: conductive lines extending along the lengths of the valve stems; connection terminals provided to one end of the valve stems and connecting to the conductive lines; current detectors provided at front ends of connecting portions to connect through valve seats to the conductive lines provided at the valve heads; current supply means for supplying a small current to the conductive lines through the lines continuously or intermittently; and a controller for turning on alarm lamps, in response to wire break detection signals from the current detectors, and at the same time stopping the fuel supply to the combustion chamber.

In this damage detecting apparatus for ceramic parts, the valves having the valve heads, such as intake and exhaust valves, have their weakest point near the connecting portion between the umbrella-shaped head portion and the valve stem and near the valve guide end. Therefore, if the valve stem fitted in the valve guide is electrically connected with the valve seat, any breakage of these components will allow an operator to immediately and sensitively detect a breakage signal. The conductive lines are connected at one end to the lines leading to the current detector and at the other end to the metal cylinder head and cylinder block.

A head liner formed in the cylinder head is formed with valve seats, the valve seats and the head liner are formed with a conductive coating layer, and the conductive lines of one valve are connected to conductive lines of another valve through the conductive coating layer.

The conductive lines are formed by impregnating or coating conductive SiC fibers embedded in the valve stems in the longitudinal direction thereof with a conductive material of TiC, ZrC, WC, $ZrB_2$, $TiB_2$, $HfB_2$, $NbB_2$, $TaB_2$ or TiN so that the SiC fibers and the conductive material are brought into contact with each other on the valve stems or valve seats.

Alternatively, the conductive lines may be formed by applying a conductive coating layer of the above-mentioned conductive material to the longitudinal outer surface of the valve stem made of the SiC fibers.

The sensitivity of the conductive lines can be controlled by the ratio of an additive $ZrB_2$ to the base material SiC to which it is added. For example, by changing the amount of $ZrB_2$ added to SiC, the temperature coefficient of resistance changes from a positive to a negative value. That is, when the amount of $ZrB_2$ added to SiC is set to about 30%, the wires will not easily pass current at elevated temperatures. When the amount of the additive is set at around 10%, the wires will easily pass current at elevated temperatures, enhancing the detection sensitivity.

Further, the conductive lines extending over the entire length of the valve stems can be formed of wires 10–20 $\mu$m thick and several millimeters wide.

The coating layer over the valve stem may be provided so that the conductive lines are 10–20 $\mu$m deep and several millimeters wide. Two or more conductive lines may be formed spaced apart on the outer circumferential surface of the valve stem. In that case, connecting these wires in series allows an entire length of the valve stem to be monitored.

The method of forming the conductive lines over the outer circumferential surface of the valve stem includes sintering the formed valve stem made of ceramics such as silicon nitride, machining it, applying conductive ceramics powder to the outer circumferential surface of the valve stem, and sintering the valve stem again. Alternatively, the wires may be formed by applying or impregnating the conductive ceramics powder to the formed valve stem made of ceramics such as silicon nitride and then sintering the valve stem.

Because the damage detecting apparatus for ceramic parts is constructed as described above, the valves can be monitored for cracks or breaks at all times by passing a small current through the conductive lines continuously or intermittently. When a crack or break occurs in the valve, a wire break detection signal from the current detector turns on an alarm lamp allowing an operator to detect the trouble early and replace or repair the valve immediately, minimizing adverse effects on other components. This in turn prevents unrecoverable damages to the engine, improving durability, reliability and service life of the engine and also reducing the overall cost. Hence, the valve structure having the damage detecting apparatus is advantageously applied to the cogeneration engines.

Furthermore, the damage detecting apparatus for ceramic parts comprises: a cylinder liner made of a ceramic material; conductive lines extending spirally along the inner wall surface of the cylinder liner in the longitudinal direction; terminals provided at the upper end of the cylinder liner and connected to the conductive lines; current detectors provided in lines connecting to the conductive lines provided to the cylinder liner; current supply means for supplying a small current to the conductive lines through the lines continuously or intermittently; and a controller for turning on alarm lamps in response to wire break detection signals from the current detectors.

The conductive lines extend in two or more spirals from one end to the other end of the cylinder liner along the inner wall surface of the cylinder liner.

The conductive lines are connected at one end to the lines that extend from the connection terminals at the upper end of the cylinder liner to the current detectors and, at the other end, to the cylinder block of a metal through the terminals at the lower end of the cylinder liner.

The controller performs control to stop the supply of fuel to the combustion chamber in response to signals from the current detectors indicating that the current flowing in the conductive lines is zero.

The cylinder liner is formed mainly of $Si_3N_4$ and its sliding surface is coated or impregnated—spirally in the longitudinal direction of the cylinder liner formed body— with SiC powder mixed with at least one of TiC, ZrC, WC, TiN, $ZrB_2$, $TiB_2$, $HfB_2$, $NbB_2$ and $TaB_2$ and then sintered to form a cylinder liner sintered body, which has the conductive lines formed longitudinally on its inner wall surface.

Alternatively, the inner wall surface of the cylinder liner made of $Si_3N_4$ may be coated with a paste of SiC mixed with the above conductive materials and then sintered to form the conductive lines.

It is also possible to form spiral grooves in the cylinder liner and embed or vapor-deposit the above conductive materials in the grooves to arrange the conductive lines. Further, the conductive lines are connected at one end to the lines leading to the current detectors and at the other end to the metal cylinder head and cylinder block.

The sensitivity of the wires can be controlled by the ratio of an additive $ZrB_2$ to the base material SiC to which it is added. For example, by changing the amount of $ZrB_2$ added to SiC, the temperature coefficient of resistance changes from a positive to a negative value. That is, when the amount of $ZrB_2$ added to SiC is set to about 30%, the wires will not easily pass current at elevated temperatures. When the amount of the additive is set at around 10%, the wires will easily pass current at elevated temperatures, enhancing the detection sensitivity.

The conductive lines provided to the cylinder liner can be formed of a wire 10–20 $\mu$m thick and several millimeters wide.

Two or more conductive lines may be formed spaced apart on the inner wall surface of the cylinder liner. In that case, the conductive lines are varied in thickness and connected in parallel to monitor the amount of wear as well over the entire length of the cylinder liner.

Or, the thickness of the conductive lines formed on the cylinder liner is varied in the longitudinal direction of the cylinder liner.

Further, the conductive layer of the conductive lines provided to the inner wall surface of the cylinder liner can be changed in depth according to the level of wear of the cylinder liner. It may be formed deep where the cylinder liner is subject to heavy wear and shallow where it is subject to light wear.

Two or more conductive lines are formed on the cylinder liner and their thicknesses varied so as to detect the amount of wear of the cylinder liner according to the wire break detection signals associated with these lines. The ability to detect the amount of wear of the cylinder liner allows for the management of maintenance according to the detected level of wear, making it possible to reliably predict the timing of engine overhaul or inspection based on the level of wear of the cylinder liner. This in turn obviates the need for periodical maintenance, facilitating the maintenance and reducing the cost.

To describe in more detail, the cylinder liner gradually wears during the reciprocating motion of the piston and the shallow conductive line will break first producing a wire break detection signal, which can be used in making appropriate estimation of the engine overhaul and inspection timing as well as the timing of replacing the cylinder liner.

Because the damage detecting apparatus for ceramic parts is constructed as described above, the cylinder liner can be monitored for wear, cracks or breaks at all times by passing a small current through the conductive lines continuously. When the cylinder liner is damaged, a wire break detection signal from the current detector turns on an alarm lamp allowing an operator to detect the level of wear of the cylinder liner or its cracks or breaks and to replace the cylinder liner immediately, minimizing adverse effects on other components. This in turn improves durability, reliability and service life of the engine, reducing the overall cost.

Hence, the cylinder liner structure having the above wear sensing means can detect the level of wear of the cylinder liner and allows proper, easy maintenance management. Because of these advantages, the cylinder liner structure of this invention can be suitably applied to stationary engines such as cogeneration engines.

DETAILED DESCRIPTION OF THE EMBODIMENT

Embodiments of the damage detecting apparatus for ceramic parts will be described by referring to the accompanying drawings. This damage detecting apparatus for ceramic parts can be applied to heat-insulated gas engines having ceramic parts and used for cogeneration and to general engines and heat-insulated engines using ceramic parts.

Figure 1:
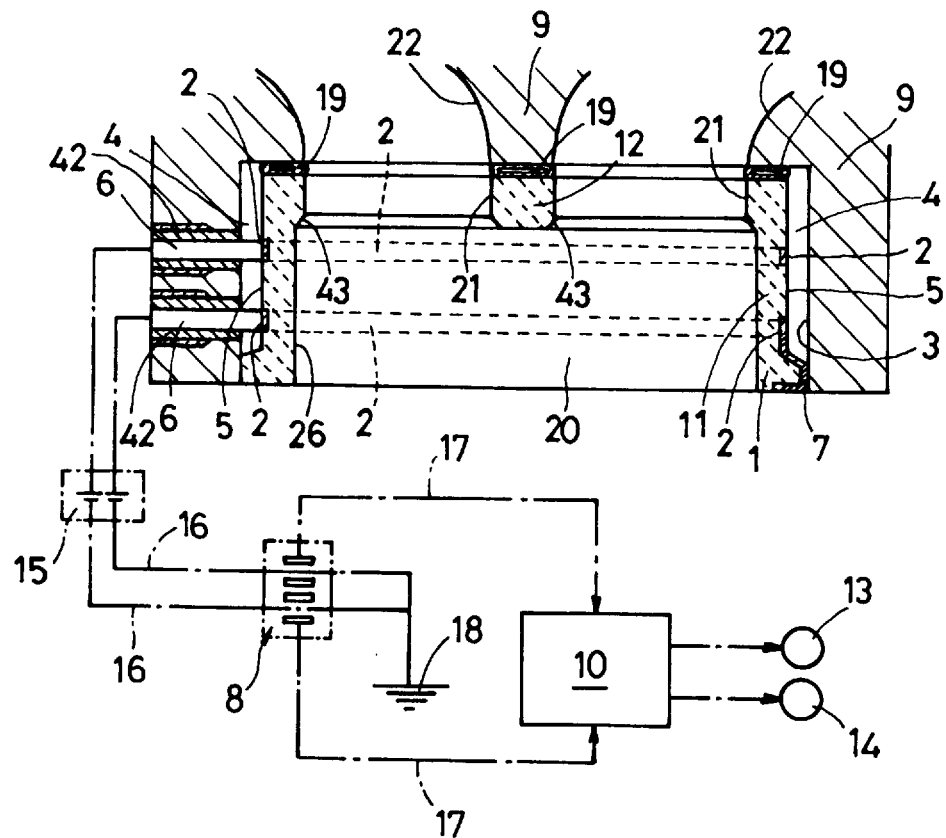
FIG. 1 is a schematic view showing a first embodiment of the damage detecting apparatus for ceramic parts.
Figure 2:
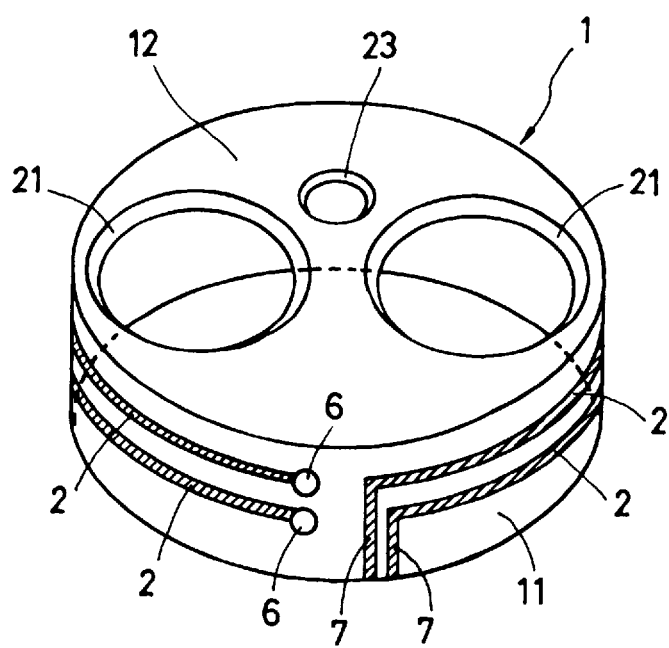
FIG. 2 is a perspective view showing a head liner in the first embodiment.

FIGS. 1 and 2 show a first embodiment of this invention as applied to the head liner that forms a combustion chamber structure used in heat-insulated gas engines and heat-insulated engines. The damage detecting apparatus for ceramic parts includes a head liner 1 installed in a cavity 3 formed in the cylinder head 9 or cylinder block; wires 2 made of conductive ceramics and arranged to extend around an entire outer circumferential surface 5 of the head liner 1; a current detector 8 provided in lines 16 connected to connection terminals 6 of the wires 2; a battery 15 as a current feeding means for supplying a small current to the wires 2 through the lines 16 at all times or intermittently; and a controller 10 which, in response to a wire break detection signal from the current detector 8, turns on an alarm lamp 13 and stops the operation of a fuel pump 14 to stop the fuel supply to a main combustion chamber 20 as the combustion chamber. The current supply to the wires 2 from the battery 15 may be continuous or intermittent such as at certain intervals or periodically and the current supply state can be checked by the current detector 8.

The head liner 1 is made of a ceramic material, such as silicon nitride and silicon carbide, by slip casting and formed as a one-piece combustion chamber structure having a head underside portion 12 and a liner upper portion 11. The head liner 1 forms a main combustion chamber 20. The head underside portion 12 is formed with ports 21 communicating with intake and exhaust ports 22 formed in the cylinder head 9. The ports 21 have valve seats 43 that accommodate intake and exhaust valves (not shown). When a fuel injection pump or a sub-combustion chamber is arranged in the cylinder head 9, they can communicate with the main combustion chamber via a through-port 23 (FIG. 2). The wires 2 are connected at one end to the connection terminals 6 and, at the other end, to the metal cylinder head 9 or cylinder block (not shown) as ground through the connection terminals 7. The connection terminals 7 may be interconnected and the connection terminals 6 taken out as a positive terminal and a negative terminal.

The connection terminals 6 are covered with insulating members 42 and installed in the cylinder head 9 to connect the wires 2 and the lines 16. The lines 16 are grounded as shown at 18. The detection signal from the current detector 8 is supplied via lines 17 to the controller 10. Below the cylinder head 9 is provided a cylinder block, not shown, which has a hollow portion in which a cylinder liner forming a cylinder 26 is installed. The cylinder 26 is formed of the head liner 1 and the cylinder liner.

The head liner 1 is installed in the cavity 3 of the cylinder head 9 with a gasket 19 interposed therebetween to form a heat insulating air layer 4 in the cavity 3. Although in this embodiment two wires 2 are laid over the outer circumferential surface of the head liner 1, a single wire or three or more may be used. The wire 2 is made of a conductive ceramics containing SiC and one or more additives such as TiC, ZrC, WC, TiN, $ZrB_2$, $TiB_2$, $HfB_2$, $NbB_2$ and $TaB_2$ added to the SiC. The wires 2 can be provided over the outer circumferential surface 5 of the head liner 1 by applying or impregnating the conductive ceramics in the head liner manufacturing process. Alternatively, the wires 2 may be formed by working the outer circumferential surface 5 of the head liner 1, applying the conductive ceramics to the outer circumferential surface 5 and firing it. The wires 2 are 10–20 $\mu$m thick or deep and several mm wide.

The wires 2 are connected at one end through the connection terminals 6 to the lines 16 that extend to the current detector 8 and at the other end through the connection terminals 7 to the metal cylinder head 9 that serves as the ground. In this embodiment, the wires 2 are insulated by the heat insulating air layer 4 formed between the outer circumferential surface 5 of the head liner 1 and the wall surface of the cavity 3 of the cylinder head 9. Depending on the circumstances, the wires 2 can be insulated by covering the outer surfaces of the wires 2 with an insulating film (not shown). The combustion chamber structure with a damage detecting apparatus, in short, has the wires 2 arranged on the outer circumferential portion where cracks are likely to develop and insulated with the heat insulating air layer 4 or insulating film to detect the wire breakage state of the circumference of the head liner 1 and thus cracks and other damages to the head liner 1, if any.

Figure 3:
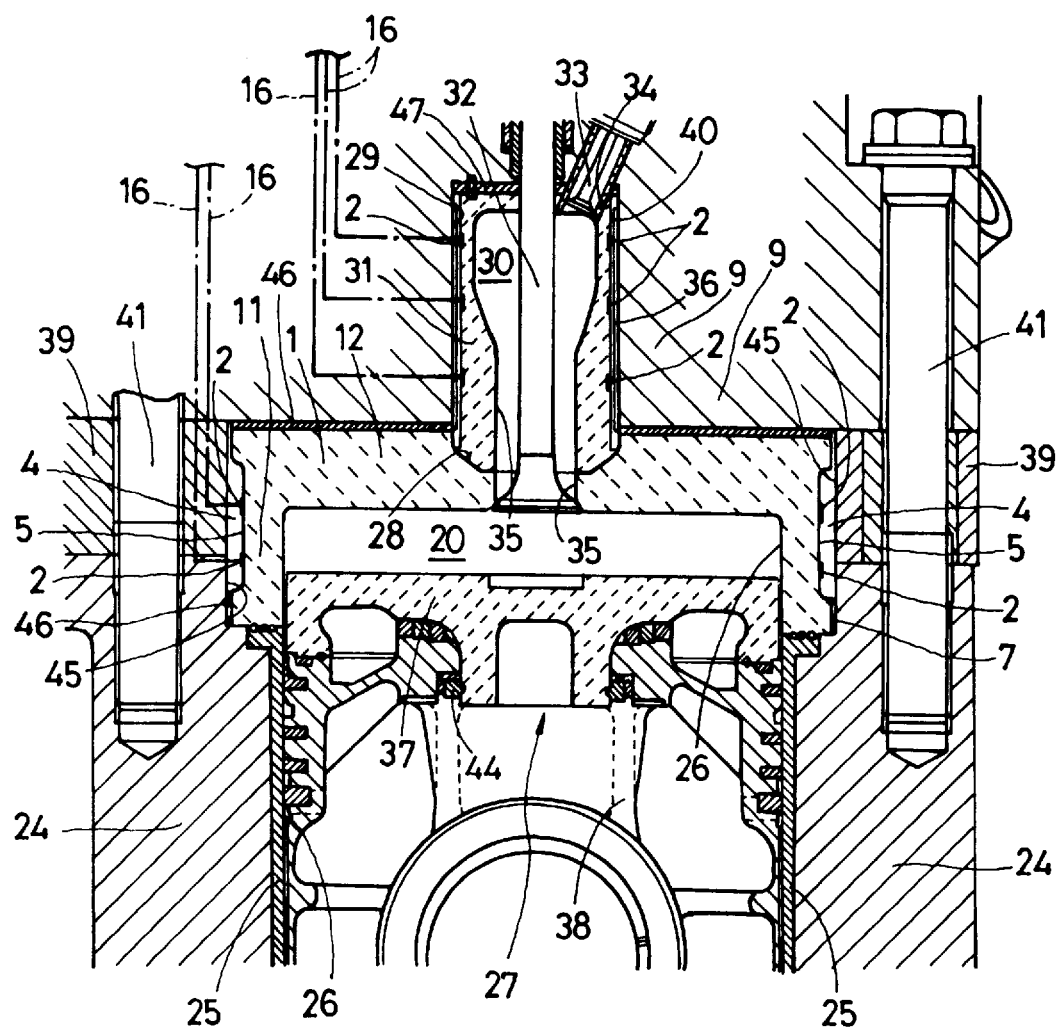
FIG. 3 is a cross section showing a second embodiment of the damage detecting apparatus for ceramic parts.

Next, by referring to FIG. 3 the second embodiment of the damage detecting apparatus for ceramic parts will be described. This embodiment is applied to a heat-insulated engine such as heat-insulated gas engine and has the same construction as the first embodiment, except that the second embodiment has a sub-combustion chamber structure in the cylinder head. Identical components with those of the first embodiment are given like reference numerals and their explanations are not repeated here.

In the second embodiment, the combustion chamber structure includes the head liner 1 forming a main combustion chamber 20 and a sub-combustion chamber structure 31 forming a sub-combustion chamber 30 that communicates with the main combustion chamber 20 through a communication hole 35, and two or more spaced-apart wires 2 are installed on the outer circumferential surface 40 of the sub-combustion chamber structure. This heat-insulated engine therefore can detect a crack or break not only in the head liner 1 but also in the sub-combustion chamber structure 31 as the preceding embodiment detects a damage of the head liner 1. The sub-combustion chamber structure 31, like the head liner 1, is made of ceramics such as silicon nitride and silicon carbide.

This heat-insulated engine has intake and exhaust ports (not shown) formed in the cylinder head 9 secured to the cylinder block 24 and also intake and exhaust valves that open and close the corresponding ports. The heat-insulated gas engine comprises a sub-combustion chamber 30 formed by a sub-combustion chamber structure 31 of a heat insulating construction installed in a cavity 29 formed in the cylinder head 9; a cylinder liner 25 fitted in a hollow portion of the cylinder block 24; a piston 27 reciprocating in a cylinder 26 formed by the cylinder liner 25; a main combustion chamber 20 of a heat insulating construction formed on the cylinder 26 side; a communication hole 35 formed in the sub-combustion chamber structure 31 to allow the main combustion chamber 20 to communicate with the sub-combustion chamber 30. Between the cylinder head 9 and the cylinder block 24 is installed an intermediate structure 39 having a hole. The cylinder head 9 is secured to the cylinder block 24 by bolts 41 with the intermediate structure 39 interposed between. The piston 27 comprises a piston head 37 made of ceramics, such as silicon nitride, with an excellent heat resistance and a piston skirt 38 secured to the piston head 37 by a connecting ring 44 through metal flow.

The main combustion chamber 20 is formed by the head liner 1, which is fitted through a gasket 46 in the hole 45 of the intermediate structure 39 mounted to the cylinder head 9. The head liner 1 has the same construction as the first embodiment. Between the wall surface of the hole 45 of the intermediate structure 39 and the outer circumferential surface 5 of the head liner 1 is formed a heat insulating air layer 4 that thermally insulates the main combustion chamber 20. Further, between the wall surface of the cavity 29 of the cylinder head 9 and the outer circumferential surface 40 of the sub-combustion chamber structure 31 is formed a heat insulating air layer 36 which thermally insulates the sub-combustion chamber 30. The head underside portion 12 is formed with a hole 28 in which the sub-combustion chamber structure 31 forming the sub-combustion chamber 30 engages. The sub-combustion chamber structure 31 is fitted in the cavity 29 of the cylinder head 9 with a gasket 47 interposed between. A communication hole 35 formed in the sub-combustion chamber structure 31 and the head liner 1 passes through the hole 28 and opens to the main combustion chamber 20. The sub-combustion chamber 30 formed in the sub-combustion chamber structure 31 is located at the center of the cylinder 26. The head underside portion 12 is formed with ports which, though not shown, communicate with the intake and exhaust ports formed in the cylinder head 9 and are provided with intake and exhaust valves.

This heat-insulated engine has a fuel supply source, not shown, containing a gas fuel such as natural gas. The cylinder head 9 is formed with a fuel supply passage 34 that communicates to a fuel supply pipe which supplies the natural gas from the fuel supply source. The natural gas—a gas fuel from the fuel supply source—is supplied through the gas fuel supply passage 34 and injected from a fuel supply port formed in the sub-combustion chamber structure 31 into the sub-combustion chamber 30. The fuel supply port is provided with a gas nozzle or fuel supply valve 33 for opening and closing the fuel supply port. The heat-insulated engine also has a communication hole valve 32 installed in the communication hole 35 to open and close the communication hole 35 that communicates the sub-combustion chamber 30 to the main combustion chamber 20. The gas fuel is supplied from the gas fuel supply source through the fuel supply pipe to the fuel supply passage 34. When the fuel supply valve 33 is operated to open the fuel supply port, the gas fuel is fed from the fuel supply passage 34 through the fuel supply port into the sub-combustion chamber 30. When the fuel supply valve 33 is operated to close the fuel supply port, the supply of gas fuel to the sub-combustion chamber 30 is stopped.

The heat-insulated engine with the above construction operates as follows. This engine repeats a sequence of four strokes—intake, compression, expansion and exhaust. In the intake stroke, the intake valve opens the intake port to introduce air into the main combustion chamber 20 and, with the communication hole 35 closed by the communication hole valve 32, the fuel supply valve 33 is operated to open the fuel supply port to supply the natural gas as the gas fuel from the gas supply source through the fuel supply passage 34 into the sub-combustion chamber 30. In the compression stroke, the communication hole 35 is still closed by the communication hole valve 32 and the air taken into the main combustion chamber 20 is compressed to a high compression ratio. Next, at the end of the compression stroke, the communication hole valve 32 opens the communication hole 35 to admit the compressed air, which is heated by high compression, from the main combustion chamber 20 into the sub-combustion chamber 30, causing the heated, compressed air to mix with the gas fuel in the sub-combustion chamber 30 and at the same time to ignite it. The combustion of the air-fuel mixture rapidly propagates, followed by flames in the sub-combustion chamber 30 ejecting out into the main combustion chamber 20 initiating the power stroke, in which the ejected burning air-fuel mixture mixes with the fresh air present in the main combustion chamber 20 completing a secondary combustion in a short period of time. In the expansion stroke, the communication hole 35 is kept open to allow the flames to be ejected from the sub-combustion chamber 30 into the main combustion chamber 20 to perform a work. Near the end of the exhaust stroke, the communication hole valve 32 is operated to close the communication hole 35.

In this heat-insulated engine, which has the communication hole 35 and the fuel supply port provided in the sub-combustion chamber 30, because the natural gas is supplied into the sub-combustion chamber 30 from the fuel supply port with the communication hole 35 closed by the communication hole valve 32 and because the air taken into the main combustion chamber 20 from the intake port is compressed during the compression stroke by the moving-up piston 27 with the communication hole 35 closed by the communication hole valve 32 to prevent the air in the main combustion chamber 20 from flowing into the sub-combustion chamber 30, the gas fuel in the sub-combustion chamber 30, even when the air in the main combustion chamber 20 is compressed to a high compression ratio, can be prevented from self-igniting and knocking as the gas fuel in the sub-combustion chamber 30 is isolated from the main combustion chamber 20 by the communication hole valve 32. When the communication hole valve 32 opens the communication hole 35, the highly compressed air flows from the main combustion chamber 20 into the sub-combustion chamber 30, mixing with the fuel gas and igniting it, rapidly burning a rich fuel mixture of a large equivalence ratio.

Now, by referring to FIGS. 4 to 7, a further embodiment of the damage detecting apparatus for ceramic parts is explained.

Figure 4:
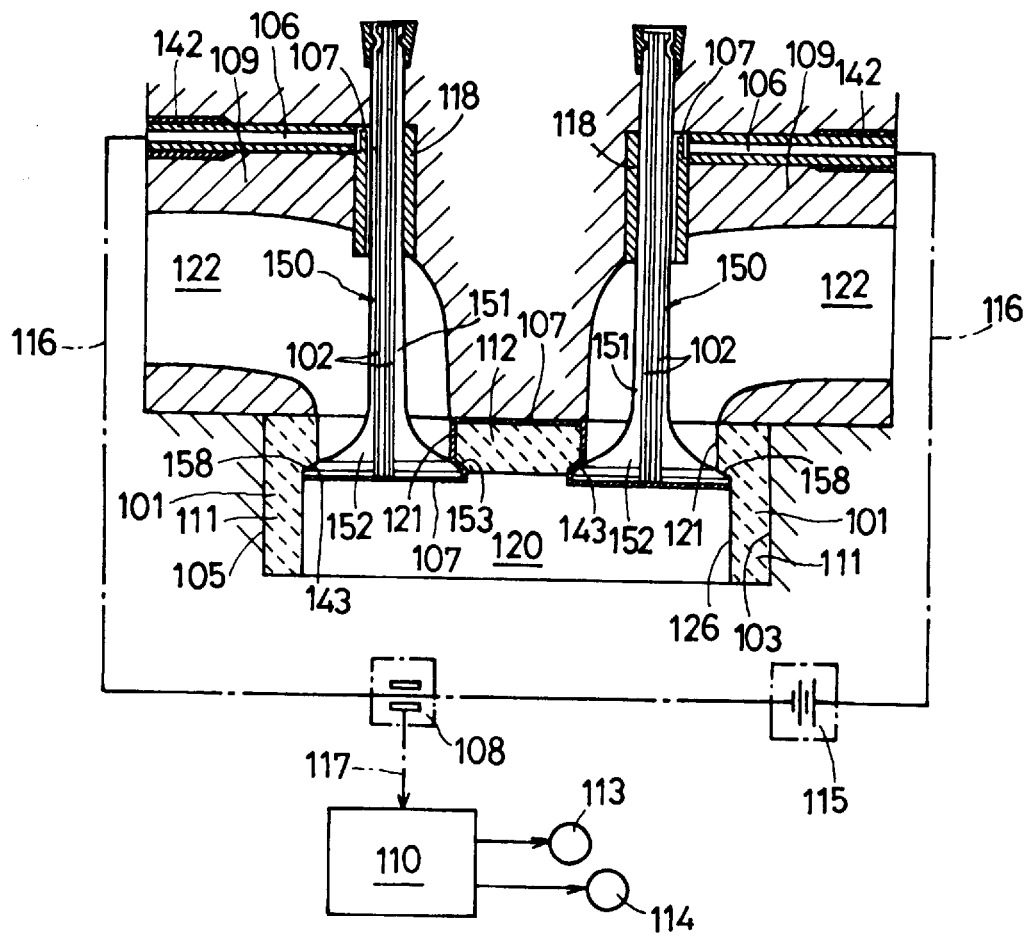
FIG. 4 is a schematic view showing a third embodiment of the damage detecting apparatus for ceramic parts.
Figure 5:
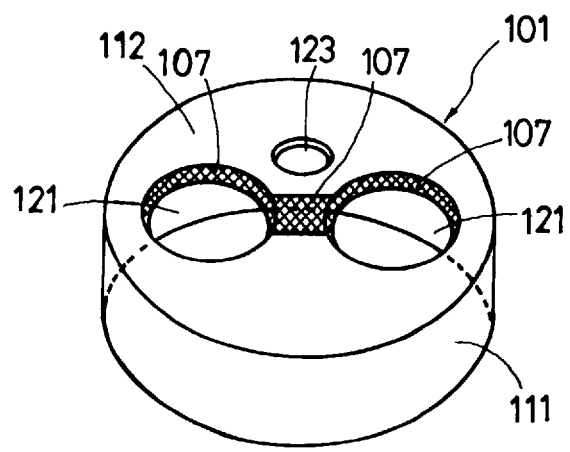
FIG. 5 is a perspective view showing a head liner in the third embodiment.

FIGS. 4 and 5 show a third embodiment of the damage detecting apparatus for ceramic parts according to this invention as applied to valves incorporated in heat-insulated gas engines and heat-insulated engines. The damage detecting apparatus for ceramic parts comprises: a head liner 101 installed in a cavity 103 formed in the cylinder head 109; valves 150 installed in ports 121 formed in the head liner 101; conductive lines 102 extending longitudinally along valve stems 151 of the valves 150; a current detector 108 provided in a line 116 connecting to connection terminals 106 of the conductive lines 102; a battery 115 as a current supply means to feed a small current to the conductive lines 102 through the line 116 continuously or intermittently; and a controller 110 which, in response to a wire break signal from the current detector 108, turns on an alarm lamp 113 and stops a fuel pump 114 to stop the fuel supply to the main combustion chamber 120. The current supply to the conductive lines 102 from the battery 115 may be continuous, or intermittent such as at predetermined intervals or periodically, and the current supply condition can be detected by the current detector 108.

The valves 150 constitute intake and exhaust valves and are formed of ceramics as a one-piece structure having a valve stem 151 and a valve head 152. The valves 150 are slidably fitted in valve guides 118 secured in the cylinder head 109. The head liner 101 has a head underside portion 112 and a liner upper portion 111 formed as an integral structure made of a ceramic material such as silicon nitride and silicon carbide. The head liner 101 forms a main combustion chamber 120. The head underside portion 112 is formed with ports 121 that communicate with intake and exhaust ports 122 formed in the cylinder head 109. The ports 121 are formed with valve seats 143 at which intake and exhaust valves 150 are installed. When a fuel injection pump or sub-combustion chamber is arranged in the cylinder head 109, they can communicate with the main combustion chamber 120 via a through-port 123 (FIG. 5).

The conductive lines 102 are connected at one end to the line 116 extending to the current detector 108 and at the other end to the metal cylinder head 109 or cylinder block (not shown) through a conductive coating layer 107 spread over the valve head 152. The connection terminals 106 are isolated from the cylinder head 109 by insulating members 142. The connection terminals 106 connect the conductive lines 102 with the line 116. A detection signal from the current detector 108 is supplied through a line 117 to the controller 110. Mounted under the cylinder head 109 is a cylinder block which, though not shown, has a hollow portion in which a cylinder liner forming a cylinder 126 is installed. The cylinder 126 comprises a head liner 101 and a cylinder liner.

In the damage detecting apparatus for ceramic parts, the conductive lines 102 provided in the valve stem 151 are formed of SiC fibers applied with a conductive material inside the valve stem 151. While FIG. 4 shows two conductive lines 102 in each valve stem 151, a single wire or three or more may be installed, spaced apart. The conductive layer forming the conductive lines 102 is an SiC layer impregnated or coated with a conductive material containing at least one of TiC, ZrC, WC, TiN, $ZrB_2$, $TiB_2$, $HfB_2$, $NbB_2$ and $TaB_2$. The conductive lines 102 can be formed during the process of manufacturing the valves 150 by impregnating a conductive ceramics into, or applying it over, a formed body of SiC fiber material embedded in the formed valve stem 151 of the valve 150.

The valve 150 is fabricated, for example, by impregnating the above-mentioned conductive material into the SiC fibers to be embedded in the formed valve, arranging a bundle of the impregnated fibers longitudinally in the valve stem 151, forming a valve with the impregnated fibers exposed at the upper end of the valve stem 151, the valve head 152 and the valve face 153, and sintering the formed valve. Further, the exposed fibers of the sintered valve are impregnated or coated with the above-mentioned conductive material to make the valve 150 a conductive body. The head liner 101 is formed with a conductive coated layer 107, which constitutes a connection terminal of the conductive lines 102 for connection with the valve 150.

In another embodiment of the damage detecting apparatus for ceramic parts, the conductive lines 102 on the valve 150 may be formed as follows. Though not shown, the conductive lines are exposed at the ends of the valve 150 as in the above embodiment. During the process of forming the valve 150, the outer surface of the valve stem 151 is impregnated or coated with the conductive material in the longitudinal direction to form the conductive lines 102 extending over the whole length of the valve stem. The conductive lines 102 may be formed into a wire 10–20 $\mu$m thick and several mm wide.

Figure 6:
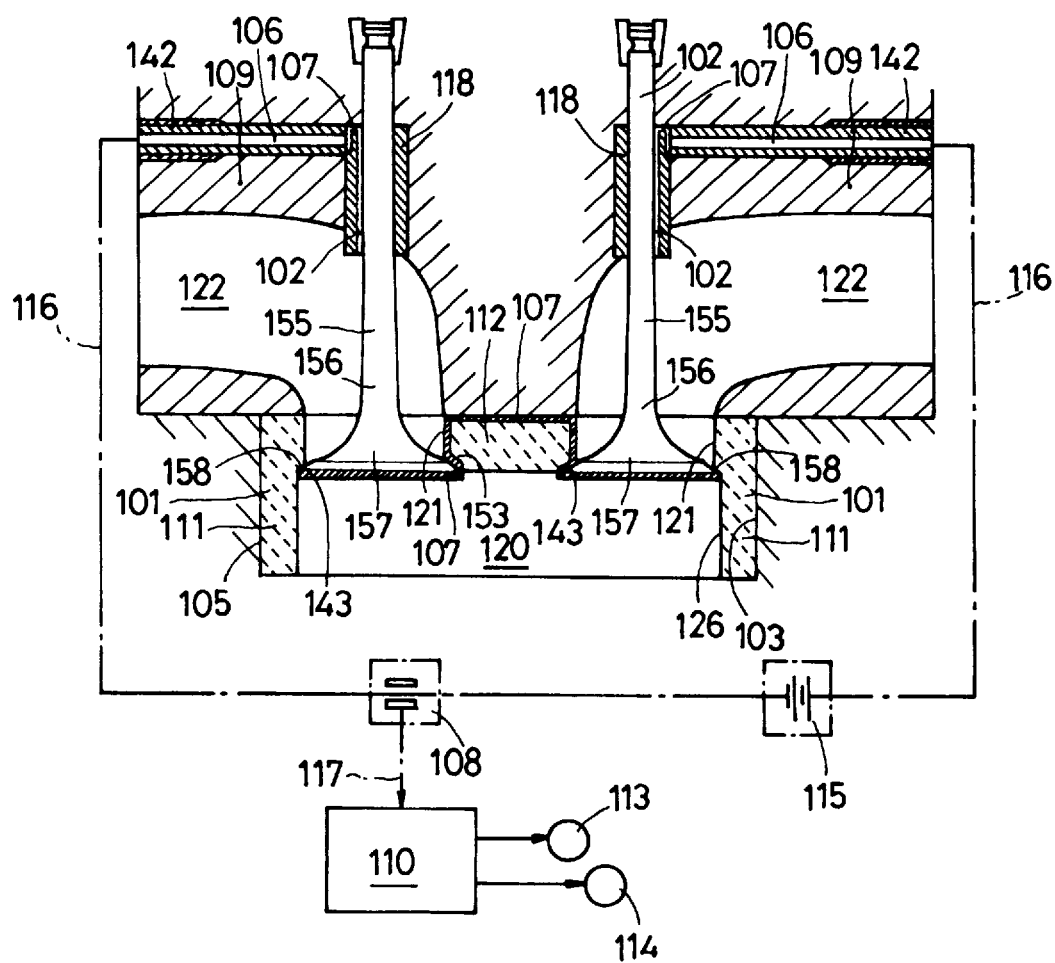
FIG. 6 is a cross section showing a fourth embodiment of the damage detecting apparatus for ceramic parts.

Next, by referring to FIG. 6, a fourth embodiment of the damage detecting apparatus for ceramic parts according to this invention will be described. The fourth embodiment is similar to the preceding embodiment of FIG. 4 except that the valve itself is made of a conductive material. Identical components are assigned the same reference numbers as in FIG. 4. In this embodiment, the conductive lines 102 provided to the valve stem 156 of the valve 155 are made by forming the valve 155 of a material which is SiC fibers impregnated or coated with a conductive material containing at least one of TiC, ZrC, WC, TiN, $ZrB_2$, $TiB_2$, $HfB_2$, $NbB_2$ and $TaB_2$. The valve 155 is formed as a one-piece structure having a valve stem 156 and a valve head 157. In this embodiment, there is no need to provide a conductive coating layer to the valve face 158 as in the embodiment of FIG. 4, because the valve face 158 is conductive.

Figure 7:
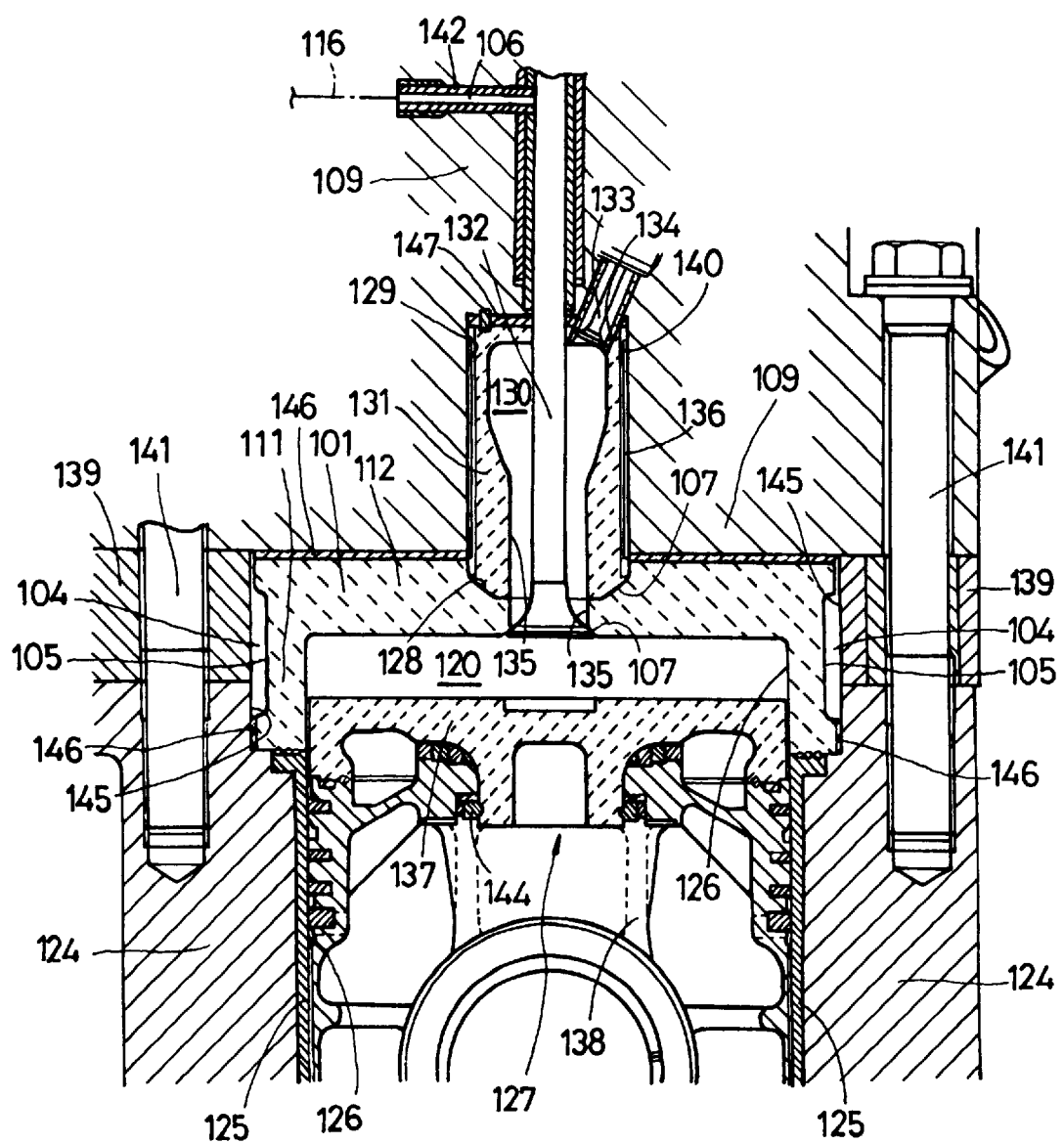
FIG. 7 is a cross section showing a fifth embodiment of the damage detecting apparatus for ceramic parts.

By referring to FIG. 7, let us explain about a fifth embodiment of the damage detecting apparatus for ceramic parts. This embodiment concerns a case where this invention is applied to a communication hole valve of the heat-insulated gas engine while the preceding embodiments concern applications to the intake and exhaust valves. The construction of the valve itself is identical with those of the receding embodiments, so the corresponding parts are given like reference numerals and their explanations omitted here.

The fifth embodiment has a head liner 101 forming the main combustion chamber 120 and a sub-combustion chamber structure 131 forming the sub-combustion chamber 130 and communicating with the main combustion chamber 120 through a communication hole 135. The main combustion chamber 120 and the sub-combustion chamber 130 communicate through the communication hole 135, which is provided with a communication hole valve 132. The communication hole valve 132 has the same structure and function as the valves 150, 155. The conductive lines 102 of the communication hole valve 132 are connected at one end to a line 116 through a connection terminal 106 and at the other end to a cylinder head 109 as ground through a conductive coated layer 107. Hence, any damages such as scores, cracks or breaks, when they develop in the communication hole valve 132, can immediately be detected.

This heat-insulated gas engine has intake and exhaust ports (not shown) formed in the cylinder head 109 secured to the cylinder block 124 and also intake and exhaust valves for opening and closing the intake and exhaust ports. The heat-insulated gas engine comprises: a sub-combustion chamber 130 formed by the heat-insulating sub-combustion chamber structure 131 installed in a cavity 129 formed in the cylinder head 109; a cylinder liner 125 fitted in the hollow portion of the cylinder block 124; a piston 127 reciprocating in the cylinder 126 formed by the cylinder liner 125; a main combustion chamber 120 of heat insulating structure formed on the cylinder 126 side; and a communication hole 135 formed in the sub-combustion chamber structure 131 to allow the main combustion chamber 120 to communicate with the sub-combustion chamber 130. In this heat-insulated gas engine, the head liner 101 and the sub-combustion chamber structure 131 are made of ceramics such as silicon nitride and silicon carbide. Between the cylinder head 109 and the cylinder block 124 is installed an intermediate structure 139 having a hole. The cylinder head 109 is secured to the cylinder block 124 by bolts 141 through the intermediate structure 139. The piston 127 comprises a piston head 137 made of ceramics such as silicon nitride with an excellent heat resistance and a piston skirt 138 secured to the piston head 137 with a coupling ring 144 through metal flow.

The main combustion chamber 120 is formed by the head liner 101 which is installed, through a gasket 146, in the hole 145 of the intermediate structure 139 mounted to the cylinder head 109. The head liner 101 has the similar construction to the above embodiment. Between the wall surface of the hole 145 of the intermediate structure 139 and the outer surface 105 of the head liner 101 is formed a heat insulating air layer 104 that thermally insulates the main combustion chamber 120. Further, between the wall surface of the cavity 129 of the cylinder head 109 and the outer surface 140 of the sub-combustion chamber structure 131 is formed a heat insulating air layer 136 that thermally insulates the sub-combustion chamber 130. The head underside portion 112 is formed with a hole 128 in which the sub-combustion chamber structure 131 forming the sub-combustion chamber 130 is fitted. The sub-combustion chamber structure 131 is fitted, through a gasket 147, in the cavity 129 of the cylinder head 109. The communication hole 135 formed in the sub-combustion chamber structure 131 and the head liner 101 passes trough the hole 128 of the head liner 101 and opens into the main combustion chamber 120. The sub-combustion chamber 130 formed in the sub-combustion chamber structure 131 is located at the center of the cylinder 126. The head underside portion 112, though not shown, is formed with ports that communicate with the intake and exhaust ports formed in the cylinder head 109 and which are provided with intake and exhaust valves.

This heat-insulated engine has a fuel supply source, not shown, containing a gas fuel such as natural gas. The cylinder head 109 is formed with a fuel supply passage 134 that communicates to a fuel supply pipe which supplies the natural gas from the fuel supply source. The natural gas, which is a gas fuel from the fuel supply source, is supplied through the gas fuel supply passage 134 and injected from a fuel supply port formed in the sub-combustion chamber structure 131 into the sub-combustion chamber 130. The fuel supply port is provided with a gas nozzle or fuel supply valve 133 for opening and closing the fuel supply port. The heat-insulated engine also has a communication hole valve 132 installed in the communication hole 135 to open and close the communication hole 135 that allows the sub-combustion chamber 130 to communicate with the main combustion chamber 120. The gas fuel is supplied from the gas fuel supply source through the fuel supply pipe to the fuel supply passage 134. When the fuel supply valve 133 is operated to open the fuel supply port, the gas fuel is fed from the fuel supply passage 134 through the fuel supply port into the sub-combustion chamber 130. When the fuel supply valve 133 is operated to close the fuel supply port, the supply of gas fuel to the sub-combustion chamber 130 is stopped.

The heat-insulated engine with the above construction operates as follows. This engine repeats a sequence of four strokes—intake, compression, expansion and exhaust. In the intake stroke, the intake valve opens the intake port to introduce air into the main combustion chamber 120 and, with the communication hole 135 closed by the communication hole valve 132, the fuel supply valve 133 is operated to open the fuel supply port to supply the natural gas as the gas fuel from the gas supply source through the fuel supply passage 134 into the sub-combustion chamber 130. In the compression stroke, the communication hole 135 is still closed by the communication hole valve 132 and the air taken into the main combustion chamber 120 is compressed to a high compression ratio. Next, at the end of the compression stroke, the communication hole valve 132 opens the communication hole 135 to admit the compressed air, which is heated by high compression, from the main combustion chamber 120 into the sub-combustion chamber 130, causing the heated, compressed air to mix with the gas fuel in the sub-combustion chamber 130 and at the same time to ignite it. The combustion of the air-fuel mixture rapidly propagates, followed by flames in the sub-combustion chamber 130 ejecting out into the main combustion chamber 120 initiating the expansion stroke, in which the ejected burning air-fuel mixture mixes with the fresh air present in the main combustion chamber 120 completing a secondary combustion in a short period of time. In the expansion stroke, the communication hole 135 is kept open to allow the flames to be ejected from the sub-combustion chamber 130 into the main combustion chamber 120 to perform a work. Near the end of the exhaust stroke, the communication hole valve 132 is operated to close the communication hole 135.

In this heat-insulated engine, which has the communication hole 135 and the fuel supply port provided in the sub-combustion chamber 130, because the natural gas is supplied into the sub-combustion chamber 130 from the fuel supply port with the communication hole 135 closed by the communication hole valve 132 and because the air taken into the main combustion chamber 120 from the intake port is compressed during the compression stroke by the moving-up piston 127 with the communication hole 135 closed by the communication hole valve 132 to prevent the air in the main combustion chamber 120 from flowing into the sub-combustion chamber 130, the gas fuel in the sub-combustion chamber 30, even when the air in the main combustion chamber 120 is compressed to a high compression ratio, can be prevented from self-igniting and knocking as the gas fuel in the sub-combustion chamber 130 is isolated from the main combustion chamber 120 by the communication hole valve 132. When the communication hole valve 132 opens the communication hole 135, the highly compressed air flows from the main combustion chamber 120 into the sub-combustion chamber 130, mixing with the fuel gas and igniting it, rapidly burning a rich fuel mixture of a large equivalence ratio.

Referring to FIGS. 8 to 11, a further embodiment of the damage detecting apparatus for ceramic parts according to this invention will be described.

Figure 8:
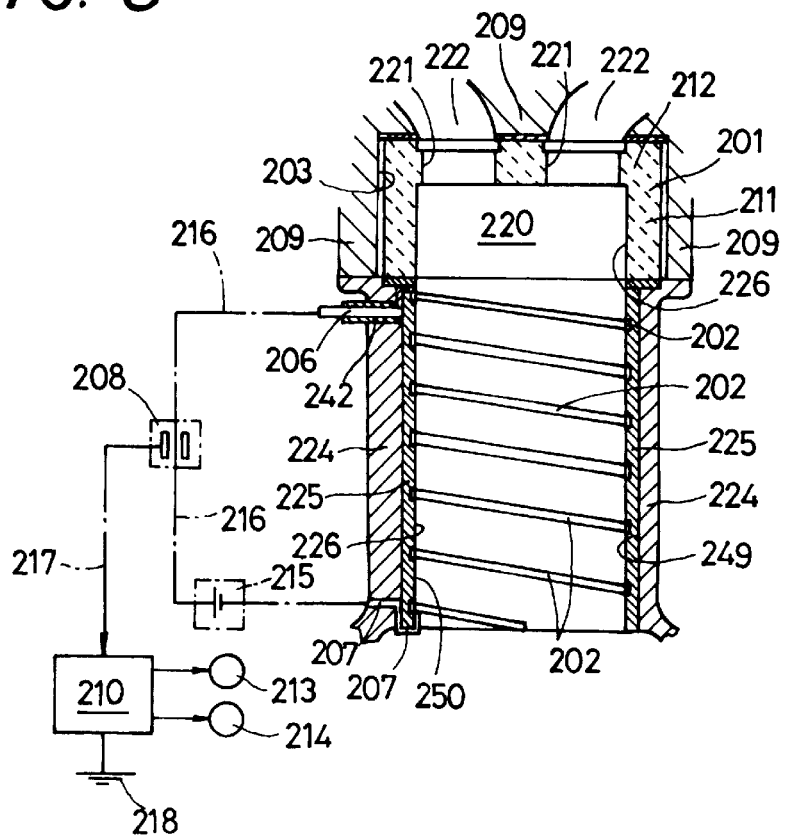
FIG. 8 is a schematic view showing a sixth embodiment of the damage detecting apparatus for ceramic parts.

FIG. 8 shows a sixth embodiment of the damage detecting apparatus for ceramic parts of this invention as applied to valves incorporated in the heat-insulated gas engines or heat-insulated engines. The damage detecting apparatus for ceramic parts comprises: a head liner 201 installed in a cavity 203 formed in the cylinder head 209; a port 221 formed in the head liner 201; a cylinder block 224 mounted to the cylinder head 209; a cylinder liner 225 made of a ceramic material and installed in the hollow portion 249 of the cylinder block 224; a conductive line 202 extending in the longitudinal direction of the inner wall surface 250 of the cylinder liner 225; a connection terminal 206 provided at the upper end of the cylinder liner 225 and connecting to a conductive line 202; a current detector 208 provided in a line 216 connecting to the conductive line 202 through the connection terminal 206; a battery 215 as a current supply means for feeding a small current to the conductive line 202 through the line 216 continuously or intermittently; and a controller 210 which, in response to a wire break detection signal from the current detector 208, turns on an alarm lamp 213 and stops a fuel pump 214 to stop the fuel supply to the combustion chamber 220. The current supply to the conductive line 202 from the battery 215 may be continuous or intermittent such as at certain intervals or periodically and the current supply state can be checked by the current detector 208. In the drawing, reference number 218 represents a ground for the controller 210.

The cylinder liner 225 is made of a ceramics such as $Si_3N_4$. The head liner 201 is made of a ceramic material such as silicon nitride and silicon carbide and formed as a one-piece structure having a head underside portion 212 and a liner upper portion 211. The head liner 201 forms the combustion chamber 220. The head underside portion 212 is formed with ports 221 which communicate with intake and exhaust ports 222 formed in the cylinder head 209 and whose valve seats are provided with intake and exhaust valves (not shown). When a fuel injection pump or sub-combustion chamber is arranged in the cylinder head 209, they can communicate with the combustion chamber 220 via a through-port.

The conductive line 202 is connected at one end to the line 216 leading to the current detector 208 and at the other end to a metal cylinder block 224 at the lower end of the cylinder liner 225. The connection terminal 206 is isolated from the cylinder block 224 by an insulating member 242. The connection terminal 206 connects the conductive line 202 and the line 216 with each other. A detection signal from the current detector 208 is fed through the line 217 to the controller 210.

In the damage detecting apparatus for ceramic parts, the conductive line 202 provided to the cylinder liner 225 is made by forming on the inner wall surface 250 of the cylinder liner 225 made from $Si_3N_4$ a conductive layer of a conductive material. While FIG. 8 shows the conductive line 202 to extend spirally from the terminal 206 at the upper end of the cylinder liner 225 to the terminal 207 at the lower end, it is possible to use one line or three or more lines 202. The conductive line 202, instead of extending spirally, may run linearly from the upper end of the cylinder liner 225 to the lower end. Further, the conductive layer of the conductive line 202 provided to the inner wall surface 250 of the cylinder liner 225 can be changed in depth according to the level of wear of the cylinder liner 225. It may be formed deep where the cylinder liner 225 is subject to heavy wear and shallow where it is subject to light wear.

The conductive layer forming the conductive line 202 is fabricated by coating or impregnating the inner wall surface 250 of the cylinder liner 225 with mixed powder, which is made by adding one of conductive materials such as TiC, ZrC, WC, TiN, $ZrB_2$, $TiB_2$, $HfB_2$, $NbB_2$ and $TaB_2$ to SiC. The conductive line 202 is formed during the cylinder liner 225 manufacturing process either by impregnating the mixed powder into the formed cylinder liner 225 or spreading it over the inner wall surface 250 and then firing the coating. Alternatively, the cylinder liner 225 may be formed with a spiral groove, in which the conductive material may be embedded or vapor-deposited to form the conductive line 202. The conductive line 202 can be formed into a wire 10–20 $\mu$m thick and several mm wide.

Figure 9:
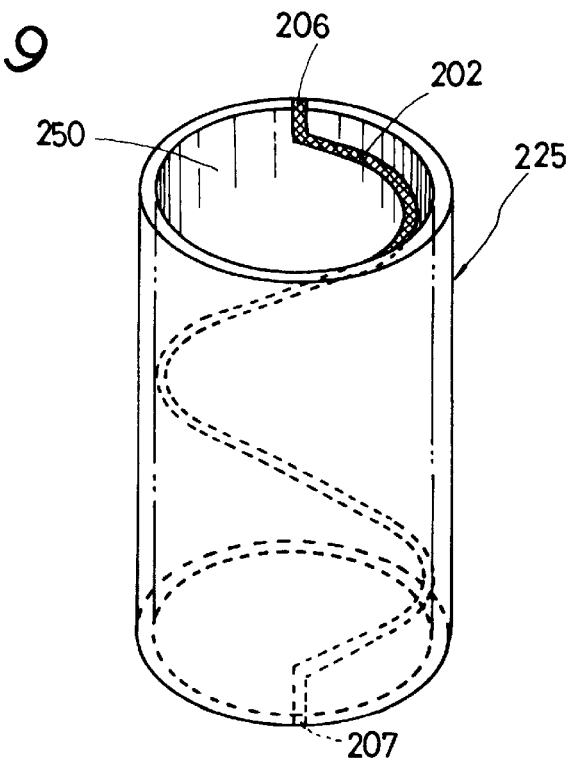
FIG. 9 is a perspective view showing a seventh embodiment of the damage detecting apparatus for ceramic parts.

Next, by referring to FIG. 9, a seventh embodiment of the damage detecting apparatus for ceramic parts according to this invention is explained. The embodiment of FIG. 7 is similar to the preceding embodiment of FIG. 8 except that the shape of the conductive line provided to the cylinder liner differs from that of the preceding embodiment. Components identical with those of the preceding embodiment are given like reference numerals. The damage detecting apparatus for ceramic parts of this embodiment has formed on the inner wall surface 250 of the cylinder liner 225 with a spiral conductive line 202 with a long lead.

Figure 10:
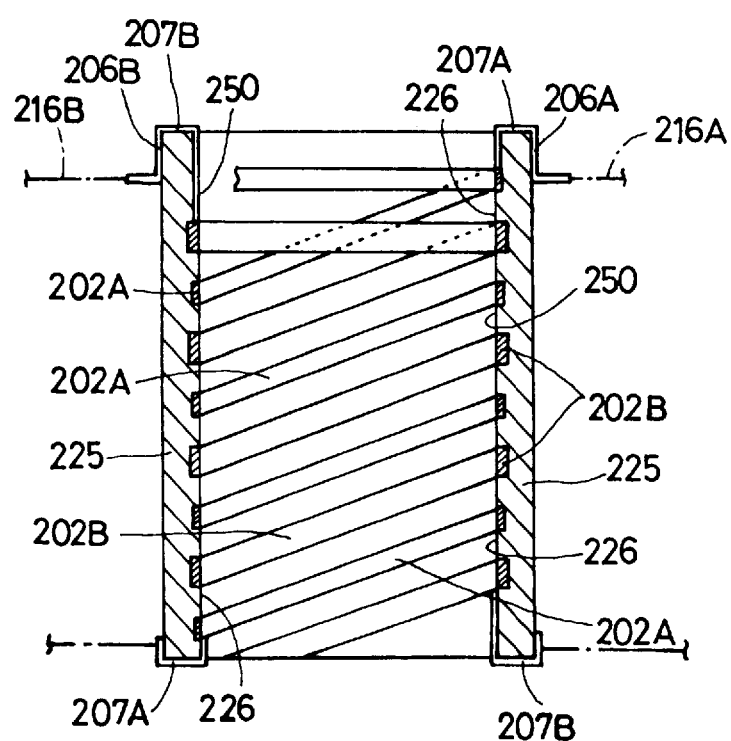
FIG. 10 is a cross section showing an eighth embodiment of the damage detecting apparatus for ceramic parts.

By referring to FIG. 10, the eighth embodiment of the damage detecting apparatus for ceramic parts according to this invention will be explained. The eighth embodiment is similar to the preceding embodiment of FIG. 8 except that the valve itself is made of a conductive material and its components identical with those of FIG. 8 are assigned like reference numerals. In this embodiment, a number of spiral conductive lines 202A, 202B (in the case of FIG. 10, two lines) with differing thicknesses or depths are formed on the inner wall surface 250 of the cylinder liner 225. The conductive lines 202A, 202B are connected to the lines 216A, 216B, respectively, so that any line break can be detected independently by the current detector 208. The conductive lines 202A, 202B are connected at one end, through connection terminals 206A, 206B, to the lines 216A, 216B, which are provided with the current detector 208. The other ends of the conductive lines 202A, 202B are connected through the connection terminals 207A, 207B to the cylinder block that serves as a ground. Hence, this embodiment allows the amount of wear of the cylinder liner 225 to be detected, making it possible to predict the life span of the cylinder liner 225 and to perform maintenance appropriately and easily, such as replacement of the cylinder liner 225.

Figure 11:
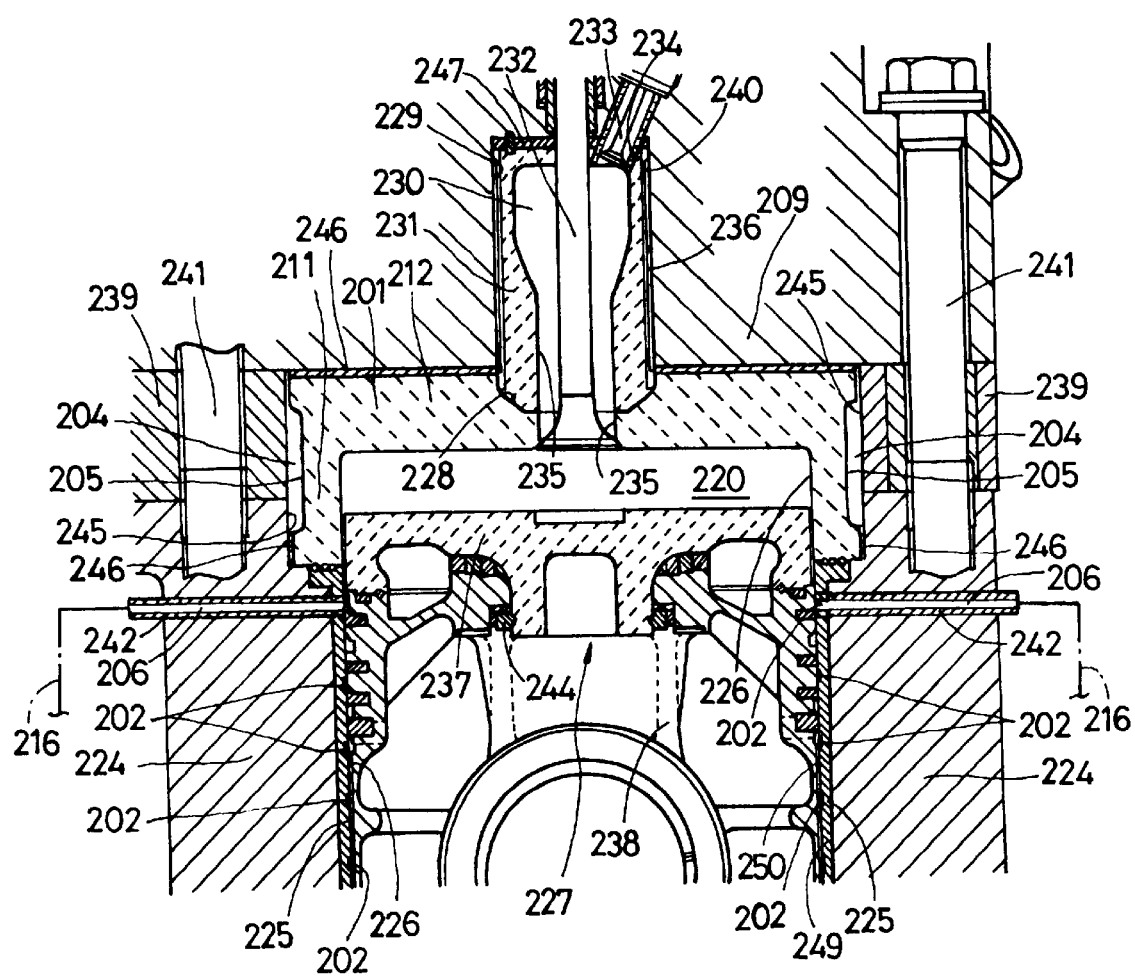
FIG. 11 is a cross section showing a ninth embodiment of the damage detecting apparatus for ceramic parts.

Further, by referring to FIG. 11, a ninth embodiment of the damage detecting apparatus for ceramic parts is described. The ninth embodiment concerns a case where the cylinder liner of the preceding embodiments is applied as the cylinder liner in the heat-insulated gas engine. The cylinder liner itself has the same construction and function as those of the preceding embodiments and thus identical parts are given like reference numerals and their explanation not repeated.

This embodiment is characterized in that the conductive line 202 is arranged on the cylinder liner 225 installed in a hollow portion 249 formed in the cylinder block 224. The conductive line 202 provided to the cylinder liner 225 has the same construction and function as the conductive line 202, 202A or 202B of the preceding embodiments. Hence, when the cylinder liner 225 develops any damages such as cracks, scores or breaks, the conductive line 202 can immediately detect them. If the conductive lines 202 with different depths (202A or 202B of FIG. 10) are formed on the cylinder liner 225, it is possible to detect the amount of wear of the cylinder liner 225.

This heat-insulated gas engine has intake and exhaust ports (not shown) formed in the cylinder head 209 secured to the cylinder block 224 and also intake and exhaust valves for opening and closing the intake and exhaust ports. The heat-insulated gas engine comprises: a sub-combustion chamber 230 formed by the heat-insulating sub-combustion chamber structure 231 installed in a cavity 229 formed in the cylinder head 209; a cylinder liner 225 fitted in the hollow portion of the cylinder block 224; a piston 227 reciprocating in the cylinder 226 formed by the cylinder liner 225; a main combustion chamber 220 of heat insulating structure formed on the cylinder 226 side; and a communication hole 235 formed in the sub-combustion chamber structure 231 to allow the main combustion chamber 220 to communicate with the sub-combustion chamber 230. In this heat-insulated gas engine, the head liner 201 and the sub-combustion chamber structure 231 are made of ceramics such as silicon nitride and silicon carbide. Between the cylinder head 209 and the cylinder block 224 is installed an intermediate structure 239 having a hole. The cylinder head 209 is secured to the cylinder block 224 by bolts 241 through the intermediate structure 239. The piston 227 comprises a piston head 237 made of ceramics such as silicon nitride with an excellent heat resistance and a piston skirt 238 secured to the piston head 237 with a coupling ring 244 through metal flow.

The main combustion chamber 220 is formed by the head liner 201 which is installed, through a gasket 246, in the hole 245 of the intermediate structure 239 mounted to the cylinder head 209. The head liner 201 has the similar construction to the above embodiment. Between the wall surface of the hole 245 of the intermediate structure 239 and the outer surface 205 of the head liner 201 is formed a heat insulating air layer 204 that thermally insulates the main combustion chamber 220. Further, between the wall surface of the cavity 229 of the cylinder head 209 and the outer surface 240 of the sub-combustion chamber structure 231 is formed a heat insulating air layer 236 that thermally insulates the sub-combustion chamber 230. The head underside portion 212 is formed with a hole 228 in which the sub-combustion chamber structure 231 forming the sub-combustion chamber 230 is fitted. The sub-combustion chamber structure 231 is fitted, through a gasket 247, in the cavity 229 of the cylinder head 209. The communication hole 235 formed in the sub-combustion chamber structure 231 and the head liner 201 passes trough the hole 228 of the head liner 201 and opens into the main combustion chamber 220. The sub-combustion chamber 230 formed in the sub-combustion chamber structure 231 is located at the center of the cylinder 226. The head underside portion 212, though not shown, is formed with ports that communicate with the intake and exhaust ports formed in the cylinder head 209 and which are provided with intake and exhaust valves.

This heat-insulated engine has a fuel supply source, not shown, containing a gas fuel such as natural gas. The cylinder head 209 is formed with a fuel supply passage 234 that communicates to a fuel supply pipe which supplies the natural gas from the fuel supply source. The natural gas—a gas fuel from the fuel supply source—is supplied through the gas fuel supply passage 234 and injected from a fuel supply port formed in the sub-combustion chamber structure 231 into the sub-combustion chamber 230. The fuel supply port is provided with a gas nozzle or fuel supply valve 233 for opening and closing the fuel supply port. The heat-insulated engine also has a communication hole valve 232 installed in the communication hole 235 to open and close the communication hole 235 that allows the sub-combustion chamber 230 to communicate with the main combustion chamber 220. The gas fuel is supplied from the gas fuel supply source through the fuel supply pipe to the fuel supply passage 234. When the fuel supply valve 233 is operated to open the fuel supply port, the gas fuel is fed from the fuel supply passage 234 through the fuel supply port into the sub-combustion chamber 230. When the fuel supply valve 233 is operated to close the fuel supply port, the supply of gas fuel to the sub-combustion chamber 230 is stopped.

The heat-insulated engine with the above construction operates as follows. This engine repeats a sequence of four strokes—intake, compression, expansion and exhaust. In the intake stroke, the intake valve opens the intake port to introduce air into the main combustion chamber 220 and, with the communication hole 235 closed by the communication hole valve 232, the fuel supply valve 233 is operated to open the fuel supply port to supply the natural gas as the gas fuel from the gas supply source through the fuel supply passage 234 into the sub-combustion chamber 230. In the compression stroke, the communication hole 235 is still closed by the communication hole valve 232 and the air taken into the main combustion chamber 220 is compressed to a high compression ratio. Next, at the end of the compression stroke, the communication hole valve 232 opens the communication hole 235 to admit the compressed air, which is heated by high compression, from the main combustion chamber 220 into the sub-combustion chamber 230, causing the heated, compressed air to mix with the gas fuel in the sub-combustion chamber 230 and at the same time to ignite it. The combustion of the air-fuel mixture rapidly propagates, followed by flames in the sub-combustion chamber 230 ejecting out into the main combustion chamber 220 initiating the expansion stroke, in which the ejected burning air-fuel mixture mixes with the flesh air present in the main combustion chamber 220 completing a secondary combustion in a short period of time. In the expansion stroke, the communication hole 235 is kept open to allow the flames to be ejected from the sub-combustion chamber 230 into the main combustion chamber 220 to perform a work. Near the end of the exhaust stroke, the communication hole valve 232 is operated to close the communication hole 235.

In this heat-insulated engine, which has the communication hole 235 and the fuel supply port provided in the sub-combustion chamber 230, because the natural gas is supplied into the sub-combustion chamber 230 from the fuel supply port with the communication hole 235 closed by the communication hole valve 232 and because the air taken into the main combustion chamber 220 from the intake port is compressed during the compression stroke by the moving-up piston 227 with the communication hole 235 closed by the communication hole valve 232 to prevent the air in the main combustion chamber 220 from flowing into the sub-combustion chamber 230, the gas fuel in the sub-combustion chamber 230, even when the air in the main combustion chamber 220 is compressed to a high compression ratio, can be prevented from self-igniting and knocking as the gas fuel in the sub-combustion chamber 230 is isolated from the main combustion chamber 220 by the communication hole valve 232. When the communication hole valve 232 opens the communication hole 235, the highly compressed air flows from the main combustion chamber 220 into the sub-combustion chamber 230, mixing with the fuel gas and igniting it, rapidly burning a rich fuel mixture of a large equivalence ratio.

What is claimed is:

1. A damage detecting apparatus, for ceramic parts for an engine, comprising:
    a ceramic combustion chamber structure installed in a cavity in the engine and including a cylinder upper surface portion and a part of a cylinder liner;
    a wire made of a conductive ceramic and arranged on an outer circumferential surface of the combustion chamber structure;
    current supply means for supplying a small current through the wires;
    a current detector coupled to the wire and the current supply means; and
    a controller comprising means to turn on an alarm lamp and stop a fuel supply to the combustion chamber structure in response to a wire break detection signal from the current detector when the wire is broken by cracking of the combustion chamber structure,
    wherein the wires are formed by embedding powdered metal in a wire portion etched in an outer circumferential surface of the combustion chamber structure.

2. The damage detecting apparatus for ceramic parts according to claim 1, wherein the wires are made of a conductive ceramics containing SiC and at least one of TiC, ZrC, WC, TiN, $ZrB_2$, $TiB_2$, $HfB_2$, $NbB_2$ and $TaB_2$ added to SiC.

3. The damage detecting apparatus for ceramic parts according to claim 1, wherein the wires are disposed on an outer circumferential surface of the combustion chamber structure by coating or impregnation.

4. The damage detecting apparatus for ceramic parts according to claim 1, wherein the cavity is in a cylinder head of the engine,
    the combustion chamber structure is a head liner of a one-piece structure having a head underside portion and a liner upper portion, and
    the head liner is installed in the cavity of the cylinder head to form a heat insulating air layer.

5. The damage detecting apparatus for ceramic parts according to claim 4, wherein
    the combustion chamber structure comprises a sub-combustion chamber and a main combustion chamber formed in the head liner, and wherein
    the subcombustion chamber communicates to the main combustion chamber through a communication hole.

6. The damage detecting apparatus for ceramic parts according to claim 1, wherein
    the wire is connected at a first end thereof through a first connection terminal to a line leading to the current detector and
    the wire is connected at a second end thereof through a second connection terminal to metal of the engine acting as a ground.

7. The damage detecting apparatus for ceramic parts according to claim 1, wherein the wires are insulated by a heat insulating layer over an outer circumferential surface of the combustion chamber structure, the heat insulating layer including at least one of air and insulating film.

8. In an engine having a cylinder head having a combustion chamber, including a valve guide and a valve port with a valve seat, and a ceramic part including a ceramic valve to open and close the port, the valve including a valve head and a valve stem, the valve head and the valve stem being integral; the valve stem being arranged to reciprocate along the valve guide; a damage detecting apparatus for the ceramic part, comprising:
    a conductive line extending along a length of the valve stem;
    a connection terminal disposed at one end of the valve stem and connecting to the conductive line;
    a connecting portion to connect through a valve seat to the conductive line at the valve head;
    current supply means for supplying a small current through the conductive line;
    a current detector for sending a wire break detection signal when the current is interrupted; and
    a controller for turning on an alarm lamp and stopping a fuel supply to the combustion chamber in response to the wire break detection signal.

9. The damage detecting apparatus for ceramic parts according to claim 8, wherein the conductive line is formed by impregnating or coating SiC fibers embedded in the valve stems in a longitudinal direction thereof with a conductive material including at least one of TiC, ZrC, WC, $ZrB_2$, $TiB_2$, $HfB_2$, $NbB_2$, $TaB_2$ and TiN, such that the SiC fibers and the conductive material are brought into contact with each other on at least one of the valve stem and the valve head.

10. The damage detecting apparatus for ceramic parts according to claim 8, wherein the conductive lines are formed by impregnating or applying a conductive material including at least one of TiC, ZrC, WC, $ZrB_2$, $TiB_2$, $HfB_2$, $NbB_2$, $TaB_2$, and TiN to a longitudinal outer circumferential surface of the valve stem.

11. The damage detecting apparatus for ceramic parts according to claim 10, wherein the conductive lines extend over an entire length of the valve stem and are formed of wires 10–20 $\mu m$ thick and several millimeters wide.

12. The damage detecting apparatus for ceramic parts according to claim 8, wherein the conductive lines are formed by making the valve of a material comprising SiC fibers impregnated or coated with a conductive material including at least one of TiC, ZrC, WC, $ZrB_2$, $TiB_2$, $HfB_2$, $NbB_2$, $TaB_2$ and TiN.

13. The damage detecting apparatus for ceramic parts according to claim 8, wherein the conductive line is connected at one end thereof to the current detector and at another end thereof to metal of the cylinder head.

14. The damage detecting apparatus for ceramic parts according to claim 8, including a first ceramic valve and a second ceramic valve and a first valve seat and a second valve seat, and wherein a head liner in the cylinder head is formed with a conductive coating layer electrically connecting the first valve seat and the second valve seat, whereby a first conductive line of the first ceramic valve a second conductive line of the second ceramic valve are electrically connectable through the conductive coating layer.

15. A damage detecting apparatus for ceramic parts comprising:

a cylinder liner for a combustion chamber, the cylinder liner being made of a ceramic material and having an inner wall surface;

a conductive wire extending along the inner wall surface of the cylinder liner in a longitudinal direction of the cylinder liner;

a connection terminal provided at an upper end of the cylinder liner and connected to the wire;

current supply means for supplying a small current through the connection terminal and the wire;

a current detector for sending a wire break detection signal when the current is interrupted by a wire break; and a controller for turning on an alarm lamp in response to the wire break detection signal.

16. The damage detecting apparatus for ceramic parts according to claim 15, wherein the wire is formed by impregnating or applying a conductive material including at least one of TiC, ZrC, WC, $ZrB_2$, $TiB_2$, $HfB_2$, $NbB_2$, $TaB_2$ and TiN on the inner wall surface of the cylinder liner.

17. The damage detecting apparatus for ceramic parts according to claim 15, wherein the wire is 10–20 $\mu$m thick and at least one millimeter wide.

18. The damage detecting apparatus for ceramic parts according to claim 15, wherein the wires extend in two or more spirals from one end to the other end of the cylinder liner along the inner wall surface of the cylinder liner.

19. The damage detecting apparatus for ceramic parts according to claim 15, wherein the wire is connected at one end to a line extending from the connection terminal to the current detector and at the other end to a metal cylinder block, acting as a ground, through a second terminal at the lower end of the cylinder liner.

20. The damage detecting apparatus for ceramic parts according to claim 15, including a plurality of wires and wherein the wires differ in thickness along the longitudinal direction of the cylinder liner.

21. The damage detecting apparatus for ceramic parts according to claim 15, wherein the wire is formed in two or more strips and changes in thickness whereby an amount of wear of the cylinder liner can be detected by wire breakage.

22. The damage detecting apparatus for ceramic parts according to claim 15, wherein the controller includes means to stop a supply of fuel to the combustion chamber in response to the wire break detection signal.

* * * * *